United States Patent
Kim et al.

(10) Patent No.: US 10,330,672 B2
(45) Date of Patent: Jun. 25, 2019

(54) METHOD FOR SCREENING ACTIVATOR OF MITOCHONDRIAL ACTIVITY

(71) Applicant: INTELLIGENT SYNTHETIC BIOLOGY CENTER, Daejeon (KR)

(72) Inventors: Sun Chang Kim, Daejeon (KR); Chan Bae Park, Gyeonggi-do (KR); Soon Jang Lee, Gyeonggi-do (KR)

(73) Assignee: INTELLIGENT SYNTHETIC BIOLOGY CENTER, Daejeon (KR)

( * ) Notice: Subject to any disclaimer, the term of this patent is extended or adjusted under 35 U.S.C. 154(b) by 0 days.

(21) Appl. No.: 15/511,997

(22) PCT Filed: Jun. 22, 2016

(86) PCT No.: PCT/KR2016/006592
§ 371 (c)(1),
(2) Date: Mar. 16, 2017

(87) PCT Pub. No.: WO2017/003124
PCT Pub. Date: Jan. 5, 2017

(65) Prior Publication Data
US 2017/0292945 A1   Oct. 12, 2017

(30) Foreign Application Priority Data
Jul. 1, 2015   (KR) .................. 10-2015-0094015

(51) Int. Cl.
*G01N 33/50* (2006.01)
*C07J 17/00* (2006.01)

(52) U.S. Cl.
CPC .......... *G01N 33/5079* (2013.01); *C07J 17/00* (2013.01); *G01N 2500/04* (2013.01)

(58) Field of Classification Search
None
See application file for complete search history.

(56) References Cited

U.S. PATENT DOCUMENTS

2006/0246163 A1   11/2006   Huh et al.

FOREIGN PATENT DOCUMENTS

| KR | 10-2005-0117313 | 12/2006 |
|---|---|---|
| KR | 10-2008-0085292 | 9/2008 |
| KR | 10-1048766 | 8/2010 |
| KR | 10-2013-0064761 | 6/2013 |
| KR | 10-2013-0069430 | 6/2013 |
| KR | 10-2014-0012456 | 2/2014 |
| WO | WO 00-44931 | 8/2000 |

OTHER PUBLICATIONS

Toth et al. J. Clin. Invest. (1984) 74: 292-295 (Year: 1984).*
Cui et al. Eur. J. Pharmaceut. Sci. (1999) 187-191 (Year: 1999).*
Luo et al. eCAM (2006) 3(3): 365-372 (Year: 2006).*
Extended European Search report issued in European Patent Application No. 16818157.6 dated Dec. 15, 2017.
Hoa, Nguyen Khanh, et al. "The possible mechanisms by which phanoside stimulates insulin secretion from rat islets." *Journal of Endocrinology* 192.2 (2007): 389-394.
Li, Lin, Li-ping Jiao, and Benjamin HS Lau. "Protective effect of gypenosides against oxidative stress in phagocytes, vascular endothelial cells and liver microsomes." *Cancer Biotherapy & Radiopharmaceuticals* 8.3 (1993): 263-272.
Liu, Chunying, et al. "Biotransformation pathway and kinetics of the hydrolysis of the 3-O-and 20-O-multi-glucosides of PPD-type ginsenosides by ginsenosidase type I." *Process Biochemistry* 49.5 (2014): 813-820.
Cui et al., "Enhanced Production of Gypenoside LXXV using a Novel Ginsenoside-transforming β-glucosidase from Microbacterium sp. Gsoil 167 Anti-cancer Activity", 42nd Annual Meeting & International Symposium, pp. 458, 2015.

* cited by examiner

*Primary Examiner* — Susan M Hanley
(74) *Attorney, Agent, or Firm* — Parker Highlander PLLC

(57) ABSTRACT

The present invention relates to a method for screening an activator of mitochondrial activity by using gypenoside-treated cells, to a composition for screening an activator of mitochondrial activity, comprising the gypenoside, and to a kit comprising the composition. By using the method for screening an activator of mitochondrial activity of the present invention, it is possible to effectively discover a preparation which can substantially promote the mitochondrial activity, and thus the method is expected to be widely used in developing a therapeutic agent for diseases caused by mitochondrial activity inhibition.

4 Claims, 2 Drawing Sheets

METHOD FOR SCREENING ACTIVATOR OF MITOCHONDRIAL ACTIVITY

This application is a national phase application under 35 U.S.C. § 371 of International Application No. PCT/KR2016/006592, filed Jun. 22, 2016, which claims priority to Korean Application No. 10-2015-0094015, filed Jul. 1, 2015, which are incorporated herein in their entirety.

TECHNICAL FIELD

The present invention relates to a method for screening an activator of mitochondrial activity. Specifically, the present invention relates to a method for screening an activator of mitochondrial activity using cells treated with gypenoside, a composition for screening an activator of mitochondrial activity, comprising the gypenoside, and a kit comprising the composition.

BACKGROUND ART

The mitochondrion is an organelle found in most eukaryotic cells. One of the major functions thereof is oxidative phosphorylation, through which energy derived from a metabolism of fuel materials such as glucose or fatty acid, etc. is converted into adenosine triphosphate (ATP). ATP is used in driving various energy-requiring biosynthesis processes and other metabolic activities. The mitochondrion includes its own DNA distinct from nuclear genomic DNA. The mitochondrial DNA is known as having a circular form and approximately 16,000 base pairs. Further, the mitochondrial DNA lacks its own repair mechanism unlike the nuclear DNA, and histones acting as DNA protectors, and thus is susceptible to mutations caused by intracellular or extracellular environments. Such mutations mostly exhibit an effect of inhibiting mitochondrial activity, whereas they may partly exhibit an effect of enhancing the same.

If the mitochondrial activity is inhibited by the mutations in the mitochondrial DNA, swelling caused by an abnormality of mitochondrial membrane potential, dysfunctions by oxidative stress by reactive oxygen species or free radicals, etc., dysfunctions by genetic factors, or dysfunction by defects in oxidative phosphorylation functions for energy production of mitochondria may occur, which are known as having potential to cause a metabolic disease, degenerative brain disease, liver dysfunction, muscle disease, immune disease, etc. In this regard, various preparations are being developed to treat such diseases caused by the inhibition of mitochondrial activity (Korean Patent No. 1048766, Korean Laid-open Patent Application Nos. 2005-0117313, 2013-0064761, 2014-0012456, etc.).

Meanwhile, when the mitochondrial DNA is mutated and the activity of mitochondria is promoted, intracellular ATP is excessively produced, and consequently cellular dysfunctions may occur, by which multiple diseases may be caused, such as various autoimmune diseases including rheumatoid arthritis, and various types of cancer. Various studies on diseases caused by the inhibition of mitochondrial activity are being conducted in terms of promoting the mitochondrial activity. Still, an appropriate activator to improve the inhibition of mitochondrial activity has not been developed. It is because, although various candidate materials have been discovered which exhibit mitochondrial function-promoting activity, they were unable to substantially promote mitochondrial function. Accordingly, necessity for developing a method to find such activators that can substantially promote the mitochondrial function emerged.

DISCLOSURE

Technical Problem

Under the background, the present inventors have studied to develop a method for finding an activator of the mitochondrial activity, and as a result, they developed a method for using candidate materials which can promote the mitochondrial activity to a level equal to or higher than gypenoside 75 as mitochondrial function activators by using gypenoside 75, which is capable of promoting the mitochondrial activity in isolated cells, as a reference material, thereby completing the present invention.

Technical Solution

An object of the present invention is to provide a method for screening an activator of mitochondrial activity using cells treated with gypenoside as a control group.

Another object of the present invention is to provide a composition for screening an activator of mitochondrial activity, comprising the gypenoside.

Still another object of the present invention is to provide a kit for screening an activator of mitochondrial activity, comprising the composition.

Advantageous Effects of the Invention

By using the method for screening an activator of mitochondrial activity of the present invention, it is possible to effectively discover a preparation which can substantially promote mitochondrial activity, and thus the method is expected to be widely used in developing a therapeutic agent for diseases caused by mitochondrial activity inhibition.

BEST MODE

Figure 1:
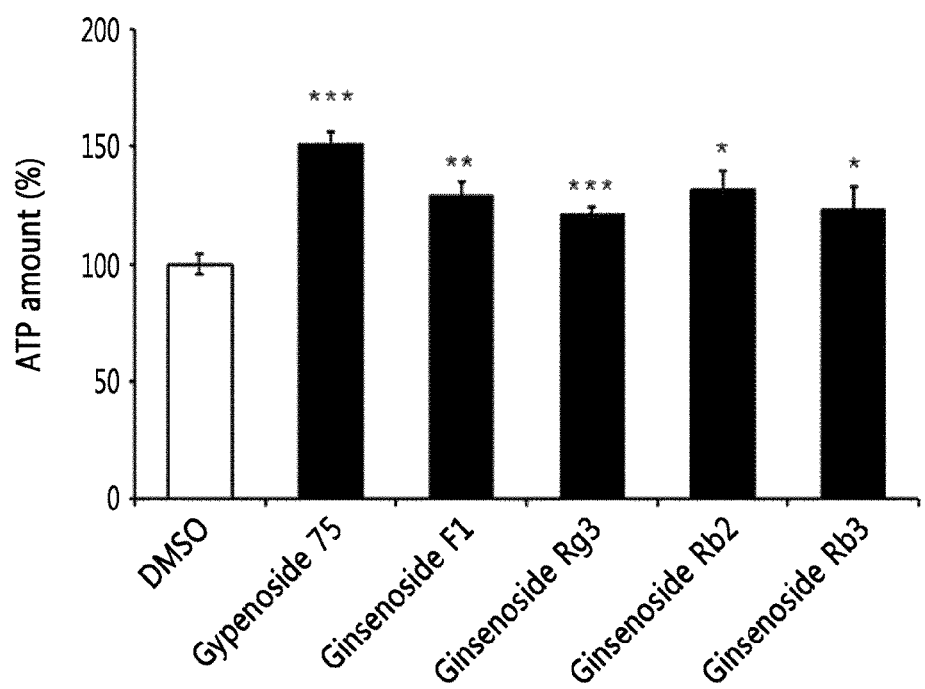
FIG. 1 is a graph illustrating changes in the intracellular ATP amount after treatments with gypenoside 75, ginsenoside F1, ginsenoside Rg3, ginsenoside Rb2, or ginsenoside Rb3.

While the present inventors conducted research in various ways to develop a method for finding an activator capable of substantially promoting mitochondrial function, they found gypenoside noticeable. Gypenoside, a compound of the saponin group, is known as being included in plants, such as *Gynostemma pentaphyllum* and *Gynostemma pentaphyllum Makino*, as well as ginseng. Further, unlike ginsenoside exhibiting various intracellular activities, gypenoside has not been known to have intracellular activity other than intracellular antioxidant activity.

The present inventors treated isolated cells with gypenoside 75 which is a type of gypenoside, and as a result of measuring changes in the amount of ATP produced in mitochondria, it was found that the amount of ATP produced increased by the gypenoside 75 treatment, and gypenoside 75 was confirmed as being an activator of mitochondrial activity capable of substantially promoting mitochondrial functions.

Therefore, in the case of screening candidate materials expected to promote mitochondrial function using cells treated with gypenoside as a control group, it was found that an activator capable of substantially promoting mitochondrial activity can be screened. Such a method for screening an activator of mitochondrial activity using gypenoside has not been disclosed, and has been developed by the present inventors for the first time.

In order to achieve the aforementioned objects, the present invention provides, as an aspect, a method for screening an activator of mitochondrial activity, comprising (a) obtaining a control group, wherein isolated cells are treated with gypenoside, and an experimental group, wherein isolated cells are treated with candidate materials expected to inhibit mitochondrial activity, respectively; (b) measuring mitochondrial activity for the control group and experimental group, respectively; and (c) selecting a candidate material, wherein mitochondrial activity measured from the experimental group exhibits a level which is higher than or equal to that from the control group.

In particular, the isolated cells are not particularly limited as long as their mitochondrial activity is promoted by gypenoside, but an example thereof may be insulin-secreting cells. The mitochondrial activity can be measured using the amount of ATP produced from mitochondria, the mitochondrial DNA level, etc. For example, if mitochondrial activity of isolated cells is enhanced after the treatment of the cells with gypenoside, the ATP production amount measured in the cells increases. Accordingly, the mitochondrial activity can be measured by measuring the amount of ATP produced from the cells of the control and experimental groups, respectively.

For a method for measuring the mitochondrial activity, all methods disclosed in the art as well as the aforementioned method can be used, and it is obvious that those skilled in the art can selectively use one of them upon necessity.

As used herein, the term "gypenoside" is also called as "gynosaponin", and refers to a dammarane-type saponin which is a type of saponin compounds included in *Gynostemma pentaphyllum* and *Gynostemma pentaphyllum* Makino. The gypenoside is known as showing various efficacies, such as improvement of lipid metabolism, prevention of cardiovascular diseases, hypoglycemic activity, activity on the central nervous system, anticancer activity, inhibition activity of platelet aggregation, tonic effect, etc., and showing antioxidant effects inside cells.

In the present invention, the gypenoside may be used as an activator of mitochondrial activity. The gypenoside is not particularly limited as long as it exhibits the effect of enhancing mitochondrial activity, and for example, gypenoside 1, gypenoside 3, gypenoside 4, gypenoside 5, gypenoside 8, gypenoside 17, gypenoside 48, gypenoside 75, etc. can be used by itself or as a combination, and as another example, it may be gypenoside 75 of Formula 1 below:

[Formula 1]

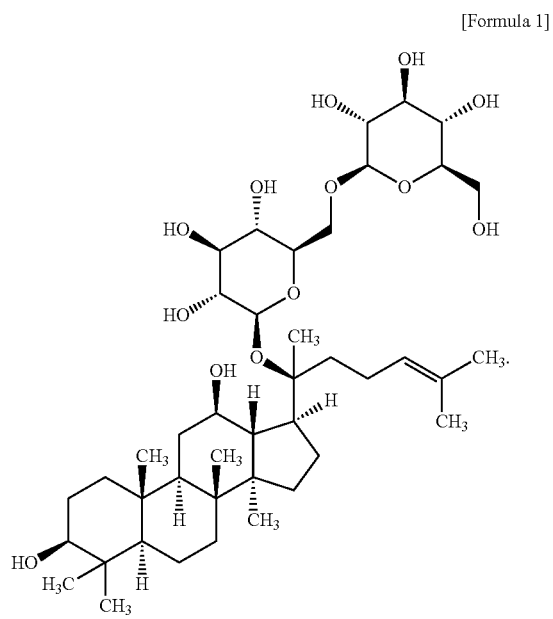

According to an exemplary embodiment of the present invention, the INS-1 cells, which are insulin-secreting cells, were treated with gypenoside 75, and were cultured for 2 hours. Then, when the amount of ATP produced by the cell was measured, the amount thereof increased, compared with cells in a control group untreated with gypenoside (FIG. 1).

Another aspect of the present invention provides a composition for screening an activator of mitochondrial activity, comprising the gypenoside, and a kit for screening an activator of mitochondrial activity, comprising the composition.

As gypenoside 75 included in the composition and kit can enhance intracellular mitochondrial activity, the composition and kit can be used for preparing a control group for screening a mitochondrial activity inhibitor.

In particular, the kit may further include, in addition to gypenoside 75, at least one type of other constitutional compositions, solutions, or devices, which are suitable for a method for determining whether a candidate material inhibits mitochondrial activity. For example, the kit may further include cells whose mitochondrial activity is enhanced by gypenoside 75, a container used for the cell culture, a medium used for the cell culture, a buffer solution used for measuring the ATP production amount, and a fluorescent material (e.g., FITC, RITC, etc.) used for measuring the ATP production amount, etc.

As a specific example, the kit of the present invention for screening an activator of mitochondrial activity may include an essential element which is necessary for conducting a luciferase assay for measuring the amount of ATP produced in mitochondria. That is, the kit may include a buffer solution for lysing a cell, luciferase, a substrate for inducing fluorescence of the luciferase, a buffer solution necessary for the fluorescence of the luciferase; and a test tube or other suitable container, etc.

As another example, the kit of the present invention for screening an activator of mitochondrial activity may include an essential element which is necessary for amplifying mitochondrial DNA by conducting Polymerase Chain Reaction (PCR). That is, the kit may include each primer pair specific for the mitochondrial DNA, a test tube or other suitable container, a reaction buffer solution (at various pHs and magnesium concentrations), deoxynucleotides (dNTPs), enzymes such as Taq polymerase and reverse transcriptase, DNase and RNAse inhibitors, DEPC-treated water, sterilized water, etc. Further, a primer pair specific for a gene used as a quantitative control group may be included.

DETAILED DESCRIPTION OF THE INVENTION

Hereinafter, the present invention will be described through an exemplary embodiment in more detail. However, the exemplary embodiment disclosed herein is only for illustrative purposes and should not be construed as limiting the scope of the present invention.

Example 1: Effect of Gypenoside 75 on Promoting Mitochondrial Activity

Lowered mitochondrial function may cause diabetes as insulin's signaling is interfered. In this regard, in order to confirm the effect of gypenoside 75 on activating the mitochondrial function, gypenoside 75 was treated, and the increased amount of ATP and mitochondrial membrane potential were measured.

Initially, the INS-1 cells, which are insulin-secreting cells, were cultured in a cell incubator (37° C., 5% $CO_2$, RPMI medium, 10% FBS), were treated with 10 μM of gypenoside 75, ginsenoside F1, ginsenoside Rg3, ginsenoside Rb2, or ginsenoside Rb3 for 2 hours, and the intracellular ATP amount and mitochondrial membrane potential were measured. For the control group, cells treated with DMSO were used.

Next, the amount of ATP was measured using luciferase. As the fluorescence by activation of luciferase depends on the amount of ATP, the intracellular ATP amount can be measured by measuring the level of the fluorescence emission.

Specifically, the INS-1 cells treated with each of the above materials were lysed through freezing-thawing and ultrasonication treatments to obtain a cell lysate. Luciferase and luciferin were added to the obtained cell lysate above to induce fluorescence, and the levels of the fluorescence were quantified and compared (FIG. 1).

FIG. 1 is a graph which shows changes in the intracellular ATP amount after the treatments with gypenoside 75, ginsenoside F1, ginsenoside Rg3, ginsenoside Rb2, or ginsenoside Rb3. As illustrated in FIG. 1, the intracellular ATP amount increased by 50% in the case of the treatment with gypenoside 75 compared with the control group.

In the final stage, the mitochondrial membrane potential was measured by tetramethylrhodamine methyl ester (TMRM) staining. As the level of the TMRM staining increases proportionately to the mitochondrial membrane potential, the intracellular mitochondrial membrane potential can be measured by measuring the level of the TMRM staining.

Specifically, the INS-1 cells treated with each of the above materials were stained with TMRM, and applied to fluorescence-activated cell sorting (FACS). Then, the level of the staining was quantified, analyzed, and compared (FIG. 2).

Figure 2:
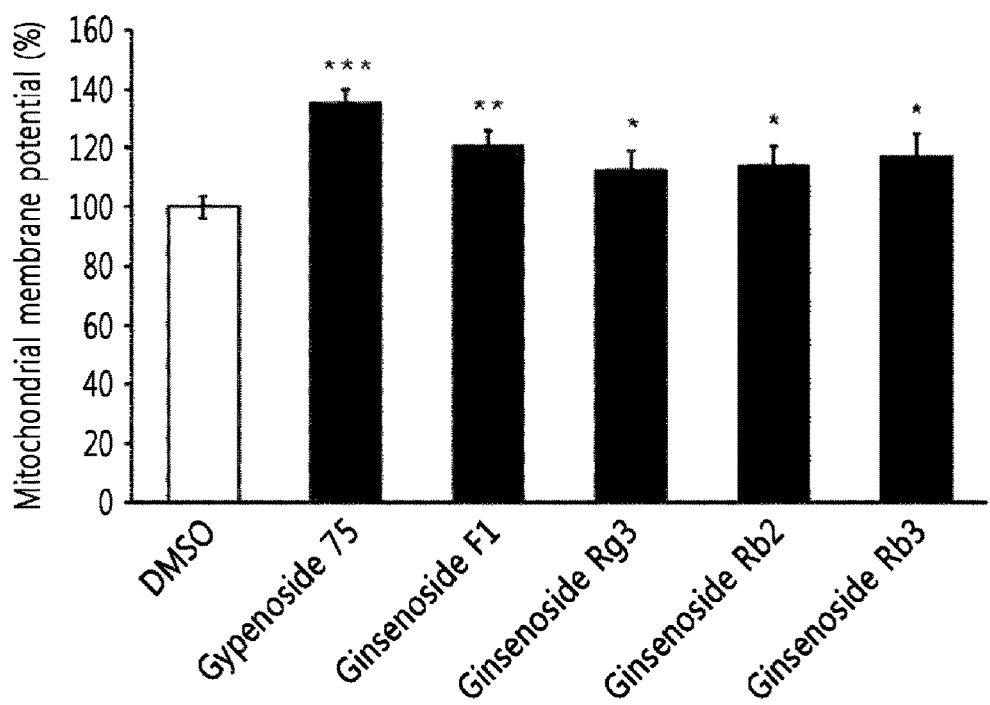
FIG. 2 is a graph illustrating changes in the mitochondrial membrane potential after treatments with gypenoside 75, ginsenoside F1, ginsenoside Rg3, ginsenoside Rb2, or ginsenoside Rb3.

FIG. 2 is a graph which shows changes in the mitochondrial membrane potential after treatments with gypenoside 75, ginsenoside F1, ginsenoside Rg3, ginsenoside Rb2, or ginsenoside Rb3. As illustrated in FIG. 2, the intracellular mitochondrial membrane potential increased by 40% in the case of the treatment with gypenoside 75 compared with the control group.

Considering the combined results of FIG. 1 and FIG. 2, gypenoside 75 activated the intracellular mitochondrial function, and increased the levels of the intracellular ATP and mitochondrial membrane potential.

INDUSTRIAL APPLICABILITY

By using the method for screening an activator of mitochondrial activity of the present invention, it is possible to effectively discover a preparation which can substantially promote the mitochondrial activity, and thus the method is expected to be widely used in developing a therapeutic agent for diseases caused by mitochondrial activity inhibition.

The invention claimed is:
1. A method for treating cells with an activator of mitochondrial activity comprising:
   (a) isolating two cell groups containing the same cell type(s);
   (b) treating a first group of cells from step (a) with a gypenoside, and treating a second group of cells from step (a) with candidate materials expected to promote mitochondrial activity, respectively; and
   (c) measuring ATP production, intracellular mitochondrial membrane potential, and/or an amount of mitochondrial DNA for the first group of cells and the second group of cells.
2. The method of claim 1, wherein the isolated cell groups are insulin-secreting cells.
3. The method of claim 1, wherein the gypenoside is any one selected from the group consisting of gypenoside 1, gypenoside 3, gypenoside 4, gypenoside 5, gypenoside 8, gypenoside 17, gypenoside 48, gypenoside 75, and a combination thereof.
4. The method of claim 1, wherein the gypenoside is gypenoside 75 Formula 1 below:

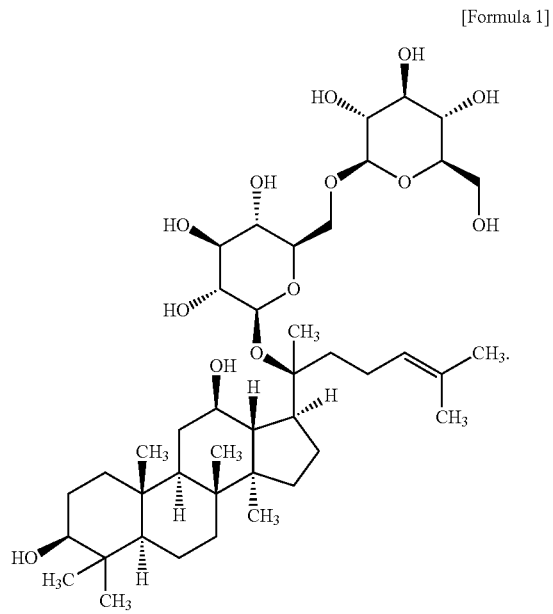

[Formula 1]

* * * * *